United States Patent
Rawles et al.

(10) Patent No.: US 6,890,316 B2
(45) Date of Patent: May 10, 2005

(54) TUBING SET FOR BLOOD HANDLING SYSTEM AND METHODS OF USE

(75) Inventors: Thomas A. Rawles, Plano, TX (US); A. Kenneth Litzie, Tustin Ranch, CA (US); David M. Fallen, Asheville, NC (US); Steven K. Stringer, Santa Clara, CA (US)

(73) Assignee: Cardiovention, Inc., Cupertino, CA (US)

( * ) Notice: Subject to any disclaimer, the term of this patent is extended or adjusted under 35 U.S.C. 154(b) by 33 days.

(21) Appl. No.: 10/134,138

(22) Filed: Apr. 25, 2002

(65) Prior Publication Data

US 2003/0204127 A1 Oct. 30, 2003

(51) Int. Cl.$^7$ .............................................. A61M 37/00
(52) U.S. Cl. ...................... 604/6.16; 604/264; 604/4.01
(58) Field of Search .............................. 604/4.01, 5.01, 604/6.01, 6.06, 6.1, 6.11, 6.14, 6.16, 7, 30–34, 264, 523, 532, 537, 538; 422/44–48; 210/645–646, 650–651, 781–782

(56) References Cited

U.S. PATENT DOCUMENTS

| | | | |
|---|---|---|---|
| 4,747,826 A | | 5/1988 | Sassano |
| 6,017,493 A | | 1/2000 | Cambron et al. |
| 6,315,751 B1 | | 11/2001 | Cosgrove et al. |
| 6,319,465 B1 | * | 11/2001 | Schnell et al. ................. 422/44 |
| 6,454,736 B1 | * | 9/2002 | Ludt et al. .................. 604/5.01 |
| 6,514,225 B1 | * | 2/2003 | Utterberg et al. .......... 604/6.16 |
| 6,602,467 B1 | * | 8/2003 | Divino et al. ................. 422/45 |
| 6,695,807 B2 | * | 2/2004 | Bell et al. ................... 604/6.16 |

OTHER PUBLICATIONS

Butler et al., "Protocols and Guidelines for Pediatric Perfusion," University of Michigan Medical Center (1998), available at <http://www.amsect.org/pediatric/protocols/mott.pdf>.

Morita et al., "Closed Circuit Cardiopulmonary Bypass with Centrifugal Pump for Open–Heart Surgery: New Trial for Air Removal," *Artificial Organs* 24(6): 442–445 (2000).

* cited by examiner

*Primary Examiner*—Angela D Sykes
*Assistant Examiner*—Leslie R. Deak
(74) *Attorney, Agent, or Firm*—Nicola A. Pisano; Luce, Foward, Hamilton & Sripps LLP

(57) ABSTRACT

A tubing set for use with a blood handling system is described that decreases the priming volume and surface area of the blood handling circuit, lowering the risk of hemodilution, platelet activation, and hemolysis. The tubing set also reduces the number of manual connections required, and uses quick-disconnect couplings to facilitate connections between the various lines, and between the lines and the arterial and venous cannulae.

16 Claims, 6 Drawing Sheets

TUBING SET FOR BLOOD HANDLING SYSTEM AND METHODS OF USE

FIELD OF THE INVENTION

The present invention relates to tubing sets configured for use with blood handling systems.

BACKGROUND OF THE INVENTION

Each year hundreds of thousands of people are afflicted with vascular diseases, such as arteriosclerosis, that result in cardiac ischemia. For more than thirty years, such disease, especially of the coronary arteries, has been treated using open surgical procedures, such as coronary artery bypass grafting. During such bypass grafting procedures, a sternotomy is performed to gain access to the pericardial sac, the patient is put on cardiopulmonary bypass, and the heart is stopped using cardioplegia solution.

Extracorporeal blood handling systems have been developed to oxygenate and circulate the patient's blood while the heart is stopped during surgery. Such systems are often complex, comprising several components, such as a blood pump, oxygenator, venous reservoir, heat exchanger, etc., coupled together by tubing. In a typical previously-known blood handling system configuration, blood is routed from a patient, e.g. from the vena cava or the right atrium, into a venous reservoir, through a blood pump, a heat exchanger, an oxygenator, a filter, and back to the patient via a cannula placed in the aorta. Each of these components, and the tubing segments connecting them, requires a minimum fluid volume to operate and presents a non-native surface area to which the patient's blood is exposed during operation of the system.

The priming volume of a blood handling system is the volume of fluid needed to purge all air from the system prior to use, i.e. to prime the system, and is equal to the total internal volume of the system. The priming fluid, for example, a sterile saline buffered solution with or without donor blood products, is typically intermixed with the patient's blood when the system is in operation. The result is hemodilution, which can decrease the concentration of critical blood components to undesirably low levels, or intermix large amounts of donor blood with the patient's own blood. Donor blood carries with it the risk of exposure to diseases carried by the blood donor.

Typical previously known blood handling systems have average priming volumes of approximately 1.8 liters, with median priming volumes of approximately 1.9 to 2.0 liters. Adding this amount of fluid can dilute the 5 liters of blood in the typical adult patient by almost one-third.

The total non-native surface area of a blood handling system is the sum of all surfaces that come into contact with the patient's blood, including the blood-accessible interior spaces of all components, the surfaces of filters and the oxygenator, and the tubing connecting the patient to the blood handling system and interconnecting the components thereof. It is known that exposure of blood to foreign surfaces is associated with platelet activation and undesirable clotting, thereby typically requiring the administration of large doses of anti-clotting agents, such as heparin. Despite this known drawback, previously known blood handling systems typically include approximately 14 $m^2$ of internal surface area.

In addition to the foregoing volume and surface area considerations, the preparation of previously known blood handling systems by the perfusionist typically requires making eight or more aseptic connections between the tubing and ports on blood handling system components. A tubing set, as used herein, refers to the segments of tubing and couplings typically used when connecting components of a cardiopulmonary bypass system.

The tubing and ports fit tightly together, and are often located in awkward and inaccessible locations, making it both physically tiresome and time consuming to make the required aseptic connections. Moreover, each of these connections represents a potential leak in the system, and air bubbles trapped at the connections can be difficult to dislodge.

Although some blood handling system suppliers have responded to the foregoing problems with pre-assembled tubing sets, these tubing sets are typically custom made in that the lengths of the various tubing segments, particularly the perfusion line, are adapted for each specific blood handling system configuration. This requirement for customization limits the ability to make a useful standardized pre-assembled tubing set.

For the foregoing reasons, it would be desirable to provide a tubing set for use with blood handling systems that provides low internal surface area and low priming volume, thereby reducing platelet activation, hemolysis and hemodilution. Preferably, such a system would reduce or obviate the need to introduce foreign fluids, such as saline or non-autologous blood, into the patient's circulation.

It further would be desirable to provide a tubing set for use with blood handling systems that requires fewer connections between the tubing set and ports on the blood handling system components, to improve both the ease of assembly and the integrity of the system once connected.

It also would be desirable to provide a standardized pre-assembled tubing set that would not need to be customized to the configuration of each blood handling system.

SUMMARY OF THE INVENTION

In view of the foregoing, it is an object of the present invention to provide a tubing set for use with a blood handling system that reduces the priming volume and internal surface area of the blood handling system, thereby reducing platelet activation, hemolysis and hemodilution.

It is another object of the present invention to provide a tubing set for use with a blood handling system that reduces the number of connections between tubing set and component ports, to facilitate assembly of the circuit including the blood handling system.

It is yet another object of the present invention to provide a standardized pre-assembled tubing set that can be used with interchangeable perfusion lines of predetermined lengths to adapt to the requirements of the configuration of each particular blood handling system, and the preferences of each clinical team.

These and other objects of the present invention are attained by providing a tubing set having a length, priming volume and internal surface area less than half that of tubing sets used in previously known blood handling systems. More preferably, the tubing set of the present invention has a length, priming volume and internal surface area less than one quarter of previously known commercial tubing sets.

In a preferred embodiment, the tubing set of the present invention comprises two circuits: a perfusion circuit and a priming circuit. The perfusion circuit couples to the inlet and outlet ports of the blood handling system, and includes venous and arterial lines. The venous and arterial lines are connected to each other during initial priming and thereafter may be joined to a perfusion line. During coupling of the blood handling system to the patient, the perfusion line is opened, either by disconnecting a preplaced connector, or by cutting the perfusion line, to create free ends. The free ends then are coupled to arterial and venous cannulae disposed in the patient's blood vessels. The perfusion circuit therefore is used to circulate the patient's blood to and from the blood handling system during surgery.

The priming circuit of the tubing set couples to the perfusion circuit at locations adjacent to the inlet and outlet ports of the blood handling system, and includes an additional tubing segment that permits priming fluid into the system during initial priming of the system. Priming fluid, which is introduced through a port at the end of the priming line, is circulated through the blood handling system to prime the system before use and to displace all air and other gasses from the system. This prevents the introduction of potential embolism-causing air bubbles into the patient's blood stream. During operation, the priming circuit also may be used to provide a recirculation loop.

In a preferred embodiment, the tubing set of the present invention comprises tubing with an internal diameter of ¼ inch, ⅜ inch, or a mixture of both, as compared with the typical previously known systems that use tubing with internal diameters of ⅜ inch, ½ inch, or a mixture of both.

The tubing set of the present invention facilitates standardization by optionally including one or more quick-disconnect tubing couplings at one or more locations in the blood handling circuit. In a preferred embodiment, quick-disconnect tubing couplings are located at the junction between the venous and arterial segments of the perfusion line and at the junction between the venous and arterial lines and the arterial and venous segments of the perfusion line, respectively. The quick-disconnect tubing connectors at the ends of the perfusion line facilitate the aseptic connection, disconnection, and reconnection of the arterial and venous lines, located outside the sterile field, to the perfusion line located within the sterile field.

The required length of the perfusion line may vary depending on the configuration of the blood handling circuit. The quick-disconnect tubing couplings at the ends of the perfusion line permit rapid, aseptic conversion among perfusion lines of various lengths, so that the rest of the tubing set may be standardized. The quick-disconnect tubing coupling between the ends of the perfusion line also may be used to facilitate aseptic connection of the venous and arterial lines to the venous and arterial cannulae, respectively, disposed in the patient's blood vessels.

In addition, to further safeguard the sterility of the perfusion line, the tubing set of the present invention may be provided in sterilized double bag packaging. In this configuration, an outer bag that encompasses the entire tubing set may be opened to reveal a second, sealed inner bag encompassing the perfusion line. This double bag packaging maintains the sterility of the perfusion line while the perfusionist connects the tubing set to the other components of the blood handling system.

The tubing set of the present invention is especially well-suited for blood handling systems having an active air removal feature, as described in co-pending, commonly assigned, U.S. patent application Ser. No. 09/780,923, filed Feb. 9, 2001. When used in conjunction with the integrated blood handling system described in that application, the entire blood handling system, including the tubing set of the present invention, comprises less than one fifth the volume and one tenth or less of the internal surface area of previously known systems.

When used with a blood handling system having the active air removal system described in the aforementioned application, a perfusionist can assemble and prime the blood processing system in a matter of minutes, as opposed to much longer periods required by previously known systems. In addition, that compact integrated blood pump/oxygenator also permits the blood handling system to be positioned just outside the sterile field, thereby reducing the length of the perfusion line required to couple the blood handling system to the arterial and venous cannulae in the patient.

The tubing set of the present invention advantageously reduces the number of connections between the tubing set and the ports of the blood handling system components. When used with the blood handling system described in the aforementioned application, the tubing set of the present invention requires only two connections to ports of the blood handling system by the perfusionist: from the venous line to the blood inlet port of the blood handling system, and from the arterial line to the blood outlet port of the blood handling system.

Methods of connecting, priming and operating a blood handling system employing the tubing set of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which.

DETAILED DESCRIPTION OF THE INVENTION

Figure 1:
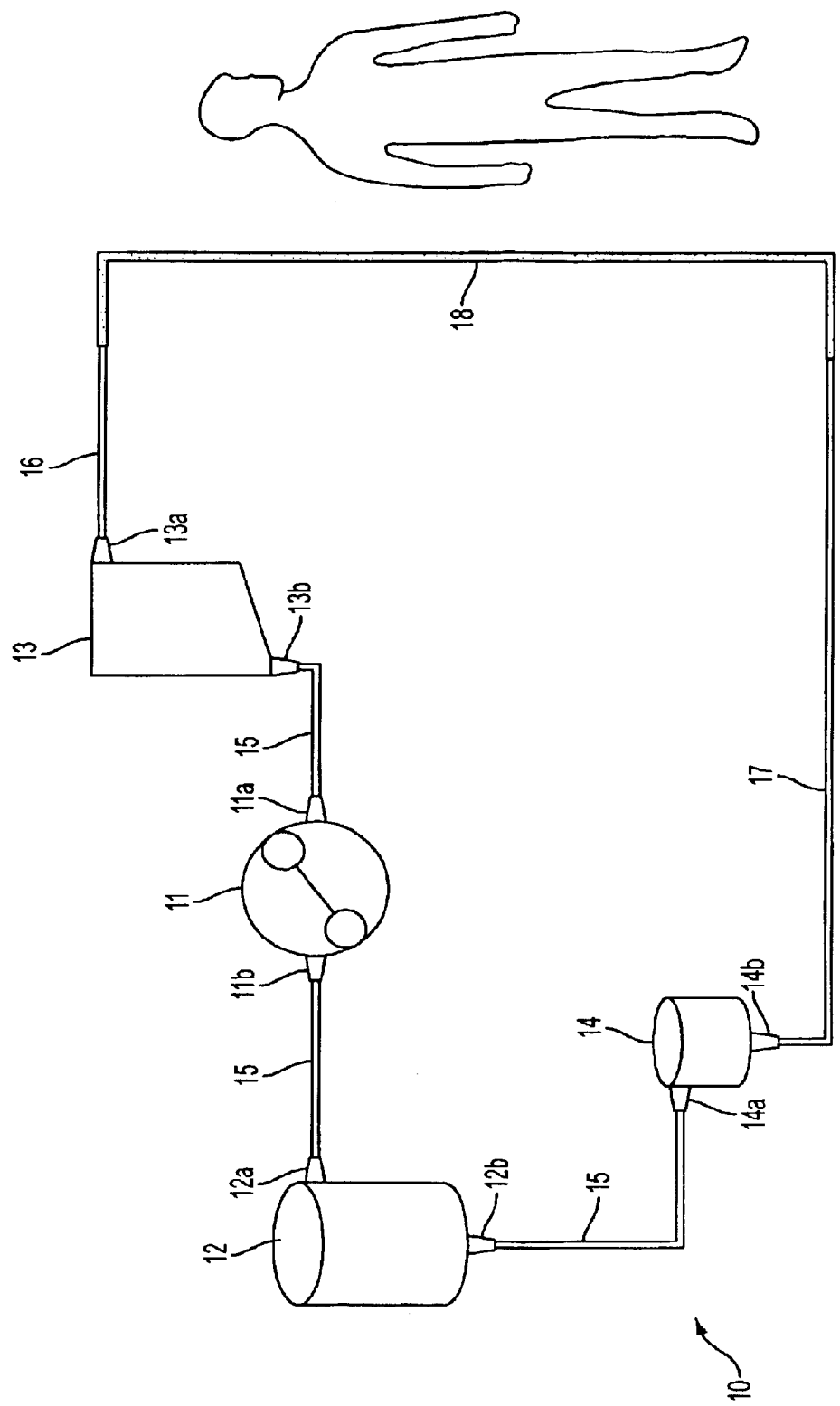
FIG. 1 is a schematic diagram of a typical previously known blood handling system and tubing set.

Referring to FIG. 1, a typical previously known commercial blood handling system 10 is described. System 10 comprises arterial pump 11, oxygenator 12, venous reservoir 13 and arterial filter 14 coupled to each other by tubing 15. To assemble such a system, the perfusionist typically removes components 11–14 from separate sterile bags, or separate compartments of a sterile tub, and then manually attaches the tubing to ports 11a, 11b, 12a, 12b, 13a, 13b and 14a, 14b, to interconnect the components and to form venous line 16 and arterial line 17. Blood handling system may in addition include a heat exchanger, recirculation line, etc. (not shown).

Typically, components 11–14 may be pole-mounted or coupled to drive units disposed in bays of the perfusion station, causing the ports of the various components to be awkwardly positioned. In addition, the conventional method of pushing the tubing over barbed or ribbed ports can be quite difficult to accomplish while maintaining these connections sterile. Venous line 16 is connected to arterial line 17 through the perfusion Line indicated by bold 18 either by connectors or as a continuum if the sizes of tubing are the same. Venous line 16, including that portion of bold line 18 that is on the venous side, as well as the pump portion of tubing 15 used to interconnect these components typically consists of ½ inch or even ⅝ inch tubing. This tubing together with arterial line 17 may have an aggregate length of 9 to 12 feet or more, and therefore a volume of one-half liter or more. The presence of additional components, such as a heat exchanger or recirculation line further add to the aggregate length, blood-contacting surface area, and priming volume.

Because the perfusion station typically is several feet distant from the operating table, it is conventional for the perfusionist to hand-up to the nurse at the operating table perfusion line, 18 in FIG. 1. The outside of all or most of this line is sterile, typically coiled and wrapped within an opaque sterilized bag. Typically, during assembly and priming of blood handling system 10, the perfusionist will attempt to prime and de-gas the perfusion line along with the balance of the blood handling system. In this case, the central portion of perfusion line 18, which is coiled, increases the difficulty in priming and de-gassing the line.

Once the perfusionist adjudges the line to be adequately primed and free of gas bubbles, the perfusionist opens the sterile bag without touching the tubing contained within and allows the coiled midsection of the perfusion line to be taken up by the nurse at the operating table, while exercising care not to contact the coil against anything. The nurse then separates arterial line 17 from venous line 16 approximately in the middle of perfusion line 18 by either cutting the perfusion line or disengaging a connector if used. The nurse and surgeon then attempt to couple the two free ends thus created to the venous and arterial cannulae disposed in the patient's blood vessels, thereby establishing a sterile connection to the venous and arterial cannulae. Alternatively, once the blood handling system is primed and de-gassed, the nurse may hand-down two separate perfusion lines to the perfusionist that are then coupled to venous and arterial lines 16 and 17, respectively. The surgeon must then wait for adequate de-airing of this line to occur before coupling the perfusion line to the cannulae.

The tubing set of the present invention is intended to solve the difficulties arising in such previously known systems, by facilitating priming and degassing of the system. In addition, the tubing set of the present invention is configured to facilitate interconnection of the blood handling system components while maintaining the sterility of the connections.

Figure 2:
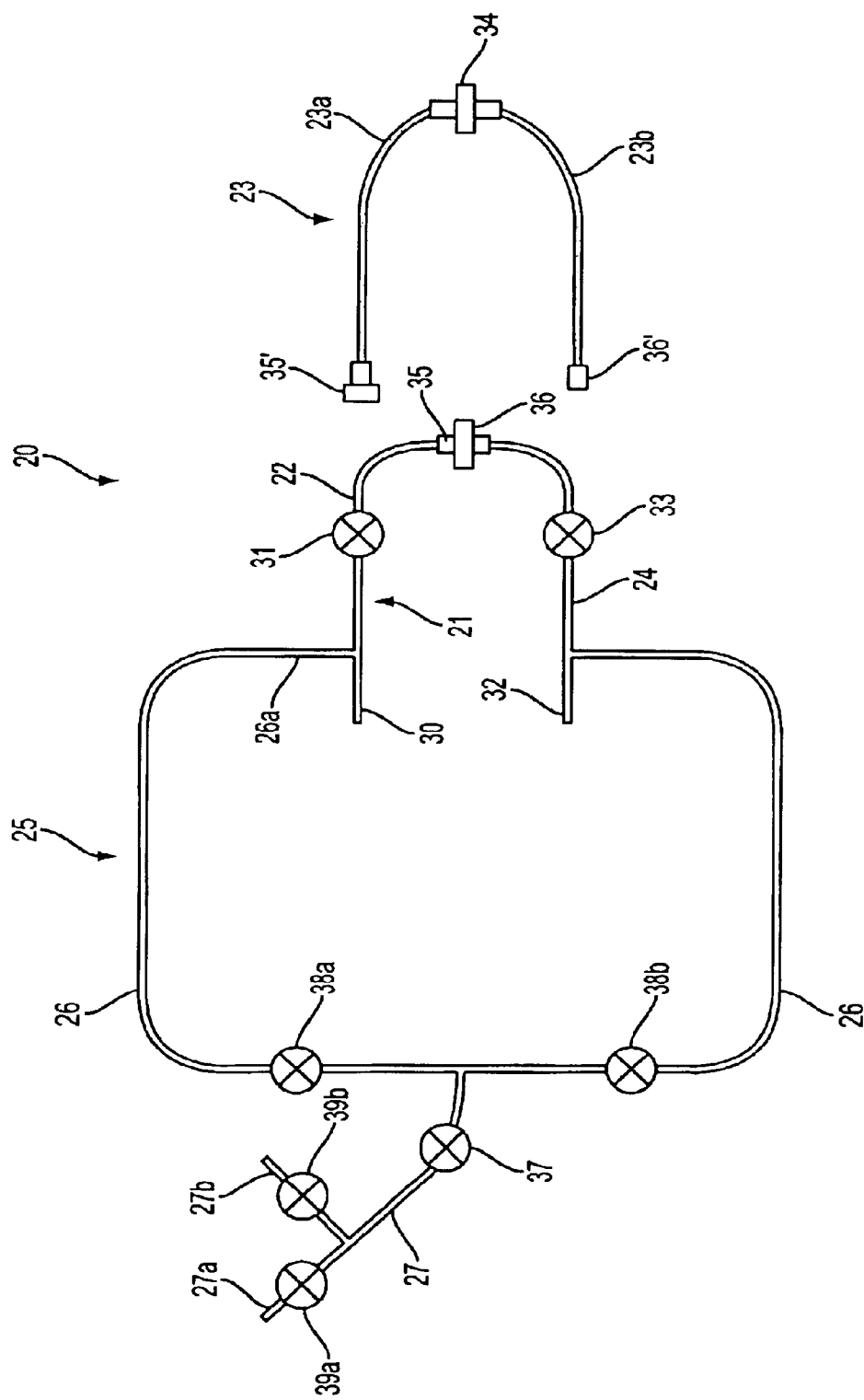
FIG. 2 is a schematic diagram of the tubing set of the present invention.

Referring now to FIG. 2, a tubing set constructed in accordance with the principles of the present invention is described. Tubing set 20 preferably comprises tubing sections arranged to form two main circuits: perfusion circuit 21, comprising lines 22, 23, 23a, 23b and 24, and priming circuit 25 comprising lines 26, 27, 27a and 27b. In a preferred embodiment, the tubing employed in perfusion circuit 21 has a ⅜ inch inner diameter, while the tubing used in priming circuit 25 has a ¼ inch inner diameter. Preferably the tubing of both the perfusion circuit and priming circuit comprises a biocompatible PVC or silicone-based polymer.

Perfusion circuit 21 is used to carry venous blood from the patient to the blood pump and oxygenator, and to return oxygenated blood from the oxygenator to the patient. During use, venous line 22 is coupled at end 30 to an inlet port of the blood pump/oxygenator and is coupled using quick-disconnect coupling half 35 to coupling half 35 of venous segment 23a of perfusion line 23. Venous line 22 may include optional valve 31, which preferably is a pinch clamp (referred to as a "Roberts clamp"). Likewise, in use, arterial line 24 is coupled at end 32 to an outlet port of blood pump/oxygenator and is coupled using quick-disconnect coupling half 36 to coupling half 36' of arterial segment 23b of perfusion line 23. Arterial line 24 also may include optional valve 33. Perfusion line 23 comprises venous segment 23a and arterial segment 23b joined by optional quick-disconnect coupler 34 having halves 34' and 34", and preferably includes quick-disconnect coupling halves 35' and 36' where it joins venous line 22 and arterial line 24, respectively. An exemplary quick-disconnect coupler is described hereinafter with respect to FIG. 7.

Priming circuit 25 is used for priming the blood pump and oxygenator during initial system set-up, and for recirculation and introduction of drugs or dilutants to the blood during operation. Line 26 is coupled at end 26a to venous line 22 of the perfusion circuit near blood pump/oxygenator inlet end 30, and is coupled at end 26b to arterial line 24 of the perfusion circuit near blood pump/oxygenator outlet end 32. Priming circuit 25 includes priming line 27, which includes suitable connections on segments 27a and 27b for joining those segments to a source of priming fluid, a source of drugs or other therapeutic agents, or a dynamic reservoir. Priming circuit preferably contains valves 37, 38a, 38b, 39a and 39b, to regulate flow through the circuit and priming line 27. Preferably, all of the valves of tubing set 20 comprise well-known pinch clamps that engage an exterior surface of the tubing.

Figure 3:
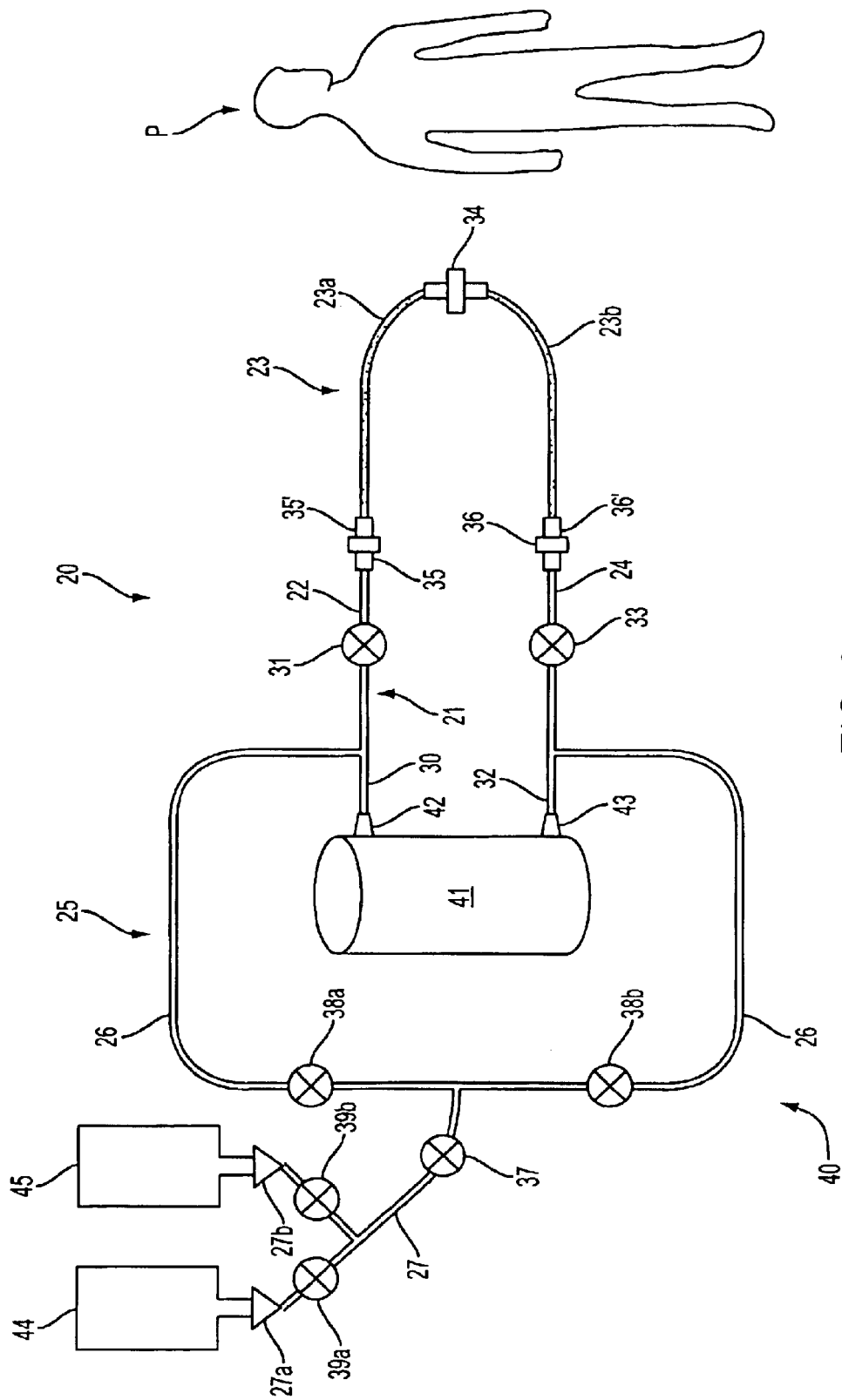
FIG. 3 is a schematic diagram showing the tubing set of the present invention coupled to an blood handling system after assembly, but prior to connection to a patient's circulatory system.

In FIG. 3, the tubing set of the present invention is depicted as it would be configured for use with the integrated blood pump/oxygenator with active air removal described in co-pending, commonly assigned U.S. patent application Ser. No. 09/780,923, although a conventional blood pump and oxygenator coupled together by tubing could be substituted therefore.

When the tubing set of the present invention is used with the integrated blood pump/oxygenator described in the aforementioned application, the entire blood handling system can be primed with as little as 400–500 ml of fluid, and has only about 1.4 $m^2$ of internal surface area. By comparison, typical previously known commercial blood handling systems require about 1.8 liters of priming fluid, and expose blood to about 14 $m^2$ of foreign surface area. The dramatic reductions in both volume and surface area facilitated by the tubing set of the present invention reduce the likelihood of adverse effects from hemodilution, platelet activation and hemolysis.

Referring to FIGS. 2 and 3, use of blood handling system 40 including tubing set 20 of the present invention is described. Tubing set 20 is shown connected to blood pump/oxygenator 41 for priming, and in FIG. 3 just prior to connection to patient P. Ends 30 and 32 of perfusion circuit 21 are coupled to inlet port 42 and outlet port 43, respectively, of blood pump/oxygenator 41. Initially, coupling halves 35 and 36 are joined together at illustrated in FIG. 2. Priming fluid, preferably buffered saline is stored in collapsible bag 44, which is coupled, e.g., by spike line, to segment 27a of priming line 27. A second collapsible sterile bag 45 may be coupled to segment 27b to serve as a dynamic reservoir once bypass flow to the patient has been established, as described hereinafter.

When valves 31, 33, 37, 38a, 38b and 39a are opened, priming fluid enters priming line 27 of the tubing set from bag 44, fills priming circuit 26, circulates through blood pump/oxygenator 41 and perfusion circuit 21. In a preferred embodiment, the valves in perfusion circuit 21 are initially closed and the bottom of bag 44 is above blood pump/oxygenator 41. Valve 39a is opened and the section of tubing above the valve deaired. Valve 37 then is opened further, priming line 27. By opening valve 38b, the flow of solution can be directed into blood pump/oxygenator 41 in a reverse direction, resulting in a more gentle displacement of air up through line 25. Valve 33 (FIG. 2) can be opened followed by valve 31 and then valve 38b to complete the priming circuit.

Blood pump 41 may be activated to pump the priming fluid throughout the system, and the active air removal system, if present, may be actuated to remove air bubbles from both priming circuit 25 and perfusion circuit 21 for venting. Alternatively, manually operable vents may be incorporated in priming circuit 25 and perfusion circuit 21 to permit the perfusionist to manually vent any air from the system. As a further alternative, the perfusion line may be opened at quick-disconnect coupling 34 to vent any accumulated air in the blood handling system.

Additional valves or vents beyond those specifically described or shown may be incorporated into any segment of tubing in the tubing set of the present invention to improve control over fluid flow and aid in purging of gas from lines or the blood handling system components. Blood handling and treatment components in addition to those shown, e.g., a blood filter or a heat exchanger, may be introduced at locations in blood handling system 40 without deviating from the scope of the present invention.

Once the priming fluid has been introduced into the blood handling system from bag 44 and any air removed from the system, valve 39a is closed, completing the set-up of the system. When the surgeon is ready to place the patient on cardiac bypass, the perfusionist closes valves 31 and 33, and then couples venous line 22 and arterial line 24 to perfusion line segments line 23a and 23b using couplings 35, 35' and 36, 36', respectively, while maintaining coupling 34 intact, as depicted in FIG. 3. Valves 30 and 31 then are opened, and blood pump/oxygenator 41 operated to prime perfusion line 23 and flush any air bubbles out of the perfusion line. Valves 30 and 31 then are closed, and the perfusionist hands perfusion line 27 up to the nurse at the operating table. The nurse receives the center portion of the perfusion line in the sterile field, uncouples quick-disconnect coupling 34, and couples the respective free ends to the arterial and venous cannulae placed in the patient's blood vessels.

Alternatively, the perfusionist may choose to close valves 31 and 33, and then couple venous line 22 to perfusion line segment 23a using couplings 35 and 35' while maintaining coupling 34 intact, as depicted in FIG. 3. Valves 31 and 39a then are opened and the head height of bag 44 or the active pump used to slowly prime line 23 just to the end of coupling 36'. Coupling 36 and 36' then are connected and valve 24 opened to complete the priming. Irrespective of sequence selected, the present invention allows the complete deairing of a large portion of perfusion circuit 21 independently of the user preference to pass line 23 up to the sterile field or vice versa.

Figure 4:
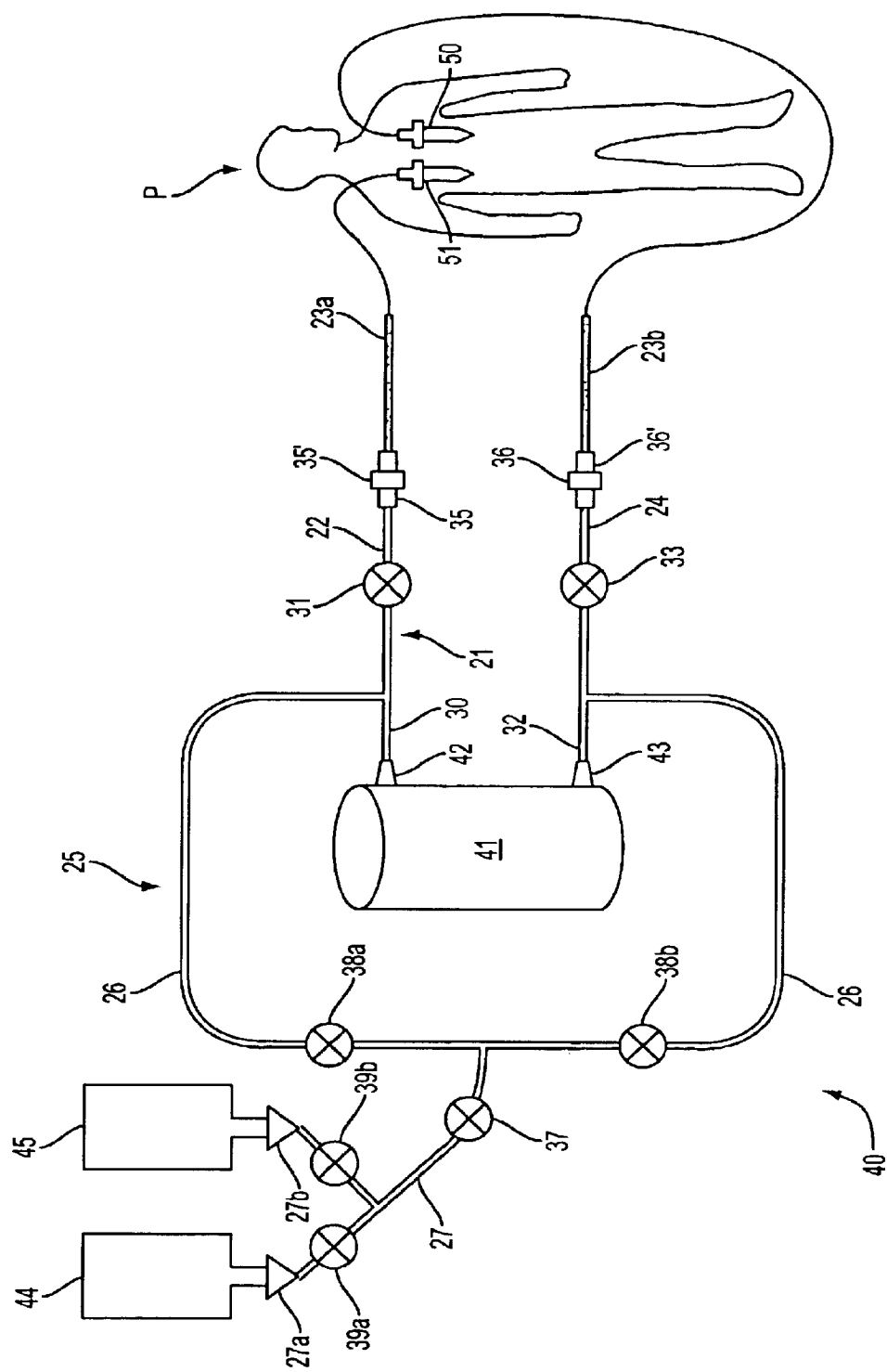
FIG. 4 is a schematic diagram the blood handling system and tubing set of FIG. 3 after connection to the circulatory system of a patient.

As illustrated in FIG. 4, arterial cannula 50 preferably is placed in the aorta or other suitable location, while venous cannula 51 preferably is placed in the patient's right atrium, vena cava, or other suitable location. When this step is completed, the perfusionist reopens valves 31 and 33, permitting blood to be circulated from the patient to the blood handling system and then reperfused into the patient. Quick-disconnect coupling halves 34' and 34" facilitate rapid, aseptic connection of venous segment 23a of perfusion line 23 to venous cannula 51 and arterial segment 23b of perfusion line 23 to arterial cannula 50, respectively.

In addition, once the blood handling system is in operation, the perfusionist may close valve 37, while leaving valves 38a and 38b open. This arrangement has the effect of causing a portion of the oxygenated blood exiting into arterial line 24 through outlet port 43 and end 32 to be recirculated to inlet port 42 of blood pump/oxygenator 41 via line 26 of the priming circuit. Also, if valve 37 is opened when valve 38a closed, a portion of the oxygenated blood exiting through outlet port 43 of blood pump/oxygenator 41 will be directed to bag 45, which will thus serve as a dynamic reservoir to temporarily accumulate blood. As a further alternative, the perfusionist may use priming line 27 to inject a drug or therapeutic agent, e.g., cardioplegia, into the blood while the perfusion loop is open, to thus directly introduce the drug or agent into patient's circulation.

Perfusion line 23 also may omit quick-disconnect coupling halves 34' and 34". In the absence of coupling 34, the surgeon may connect perfusion line 23 to the patient's circulatory system by alcohol sterilizing a mid-length of the tubing, aseptically cutting the tubing at that point, and aseptically coupling the resulting free ends to arterial cannula 50 and venous cannula 51, in accordance with previously known techniques.

Quick-disconnect coupling halves 35' and 36' also facilitate the aseptic connection of perfusion line 23, which is disposed inside the sterile field, to venous line 22 and arterial line 24, which are disposed outside the sterile field. In particular, the arrangement of the tubing set of the present invention permits the perfusion circuit and priming circuit to be manufactured with a single or a few standard lengths, while the perfusion line 23 may be provided in variable lengths to suit specific operating room configurations and surgical team preferences. Such standardization overcomes a significant shortcoming in previously known attempts to provide customized pre-assembled tubing sets, which required the hospital or clinic to stock a large inventory of entire tubing sets, rather than just the perfusion lines as is possible with present invention.

While a blood handling system incorporating the tubing set of the present invention will perform the same functions as previously known blood handling systems, the tubing set of the present invention provides a number of advantages. The low volume and surface area of a blood handling circuit including the tubing set of the present invention decreases the likelihood of adverse reactions to hemodilution or to excessive blood contact with nonnative surfaces.

The tubing set of the present invention is faster to set up and easier to use, and requires the perfusionist to make only two aseptic connections to the blood handling components. By contrast, previously known commercial blood handling systems require the perfusionist to make as many as eight or more connections. In such systems, each connection of a tube to a port must be performed aseptically, and the connections are often tight and thus physically difficult to make, especially in the often awkward locations of the ports.

In addition, the low number of connections required by the tubing set of the present invention reduces the number of locations for potential leaks, and for trapping gas bubbles, in the blood handling circuit.

Moreover, when the tubing set of the present invention is used with the integrated blood pump/oxygenator of the aforementioned patent application, only approximately 400 to 500 ml of priming fluid are required. Because an average adult patient has about 5 liters of blood, the patient's own blood may be used to prime the blood handling system, thus obviating the need for donor blood or saline. By comparison, previously known blood handling systems require about 1.8 liters of priming fluid, and thus increase the volume of the fluid in the patient's circulatory system by about one-third.

In the case where the perfusionist desires to use the patient's own blood to prime the blood handling system comprising the tubing set and integrated blood pump/oxygenator of the aforementioned patent application, the blood handling system 40 is still initially primed with saline until all air bubbles are removed from all lines and the integrated blood pump/oxygenator 41.

Once the blood pump is coupled to the arterial and venous cannulae, however, the patient's blood may be used to displace the saline, e.g., by directing the saline via valves 33, 38a, 38b, 37 and 39b to bag 45, which acts as a dynamic reservoir. When the patient's blood begins to enter arterial line 24, valves 31, 37, 38a and 39b are opened and valves 33 and 38a are closed. This procedure allows the perfusionist to prime the extracorporeal blood handling system 26 with saline, and yet never introduce the bulk of the prime saline into the patient's circulation, thus reducing hemodilution. Blood may be drawn from the patient to the blood handling system either by operation of blood pump/oxygenator 41, or more preferably, simply under the pressure provided in the patient's vessels. As will be apparent to one of skill in the art, a different arrangement of the foregoing valves may be made, so that the patient's blood is drawn into the system in a retrograde manner via arterial line 24, rather than venous line 22.

Figure 5:
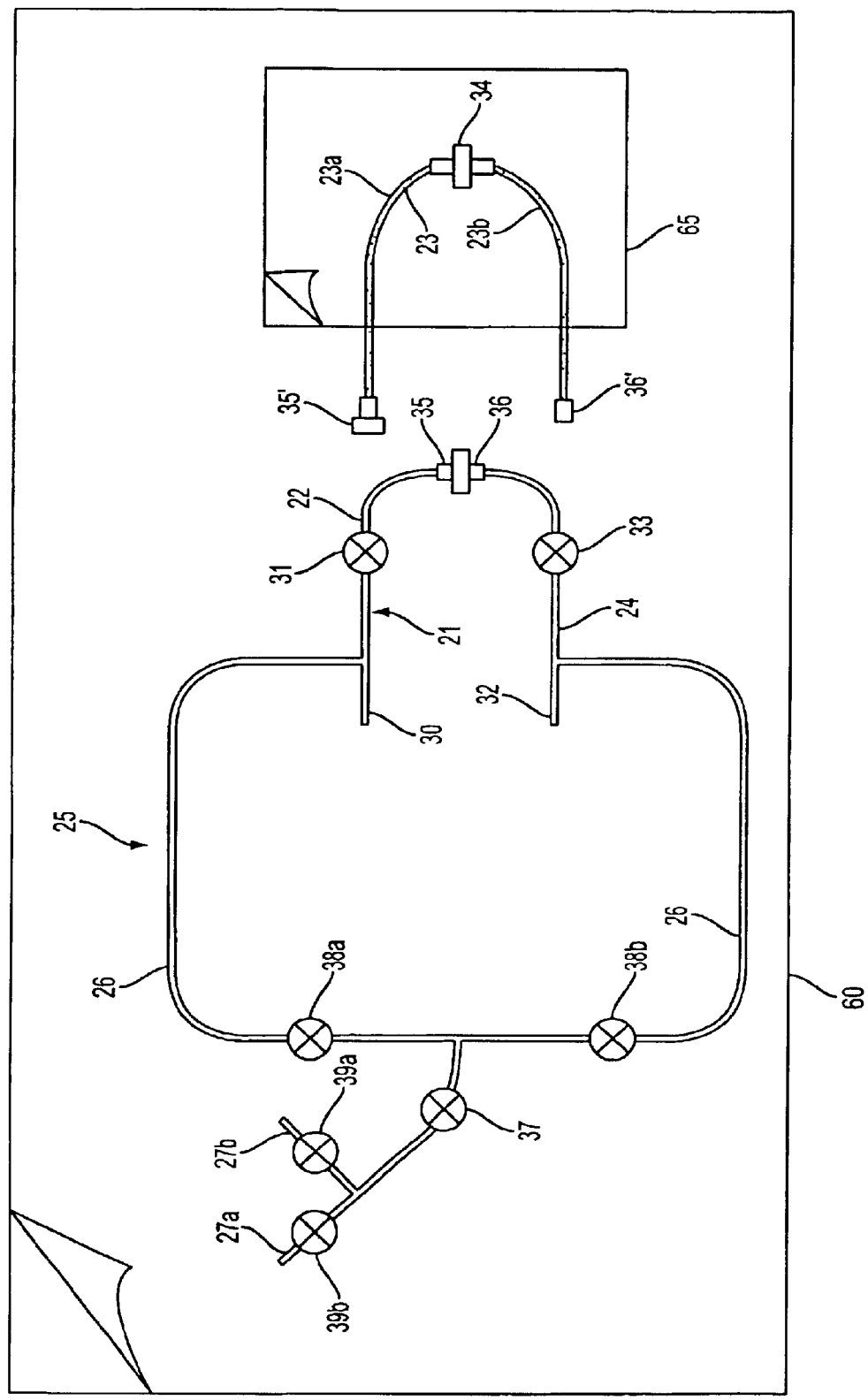
FIG. 5 is an illustration showing the tubing set of the present invention sealed in double bag packaging.

Referring now to FIG. 5, tubing set 20 of the present invention is described as packaged for commercial use. Tubing set 20 is enclosed in outer sterile bag 60, with perfusion line 23 (including quick-disconnect coupling 34, if provided) enclosed in inner sterile bag 65 with coupling halves 34' and 34" extending outside sterile inner bag 65. This arrangement permits the ends of segments 23a and 23b of perfusion line 23 to be manipulated and coupled to venous line 22 and arterial line 24 of the tubing set, while maintaining the sterility of the mid-region of perfusion line, which is handed-up to the sterile field. Tubing set 20 may be sterilized by auto-claving, irradiated, or more preferably is sterilized by exposure to ethylene oxide.

Figure 6:
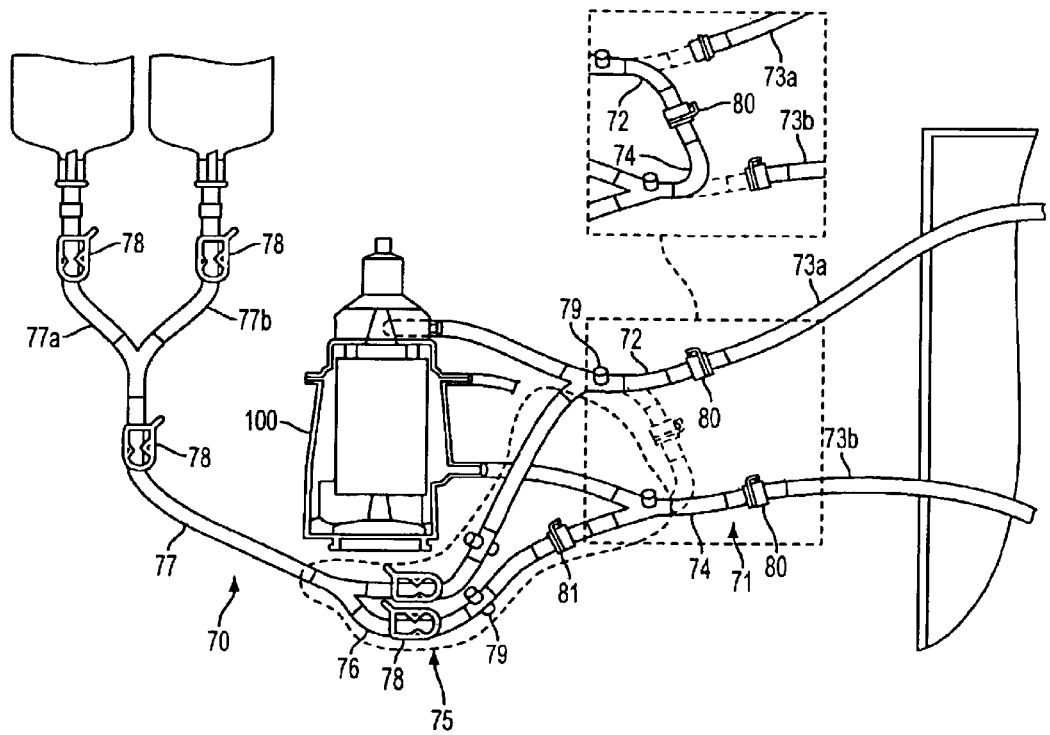
FIG. 6 illustrates a potential commercial embodiment of the inventive tubing set.

Referring to FIG. 6, an illustrative potential commercial embodiment of a tubing set constructed in accordance with the present invention is described. Tubing set 70 is shown coupled to integrated blood pump/oxygenator 100, which is described in detail in the aforementioned patent application. Tubing set 70 includes perfusion circuit 71, comprising venous line 72, perfusion line segments 73a, 73b and arterial line 74, and priming circuit 75 comprising line 76, priming line 77, and segments 77a and 77b. The ends of perfusion line segments 73a and 73b are shown extending into the sterile field as they would appear during use.

Tubing set 70 illustratively includes pinch clamps 78 and sampling manifolds 79 disposed on various of the lines. Quick-disconnect couplings 80 are shown are the junctions of venous line 72 and venous segment of perfusion line 73a and arterial line 74 and arterial segment of perfusion line 73b. As shown in the inset in FIG. 6, the quick-disconnect couplings permit venous line 72 to be directly coupled to arterial line 74 during the priming step. In addition, another quick-disconnect coupling 81 is provided in line 76 to permit, for example, the inclusion of a heat exchanger when the priming circuit is used for recirculation.

Figure 7:
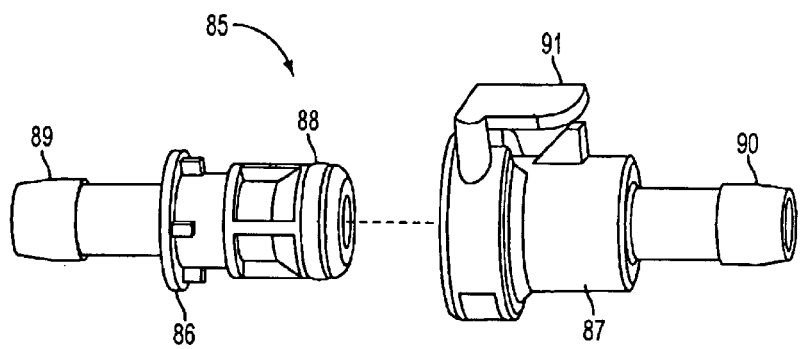
FIG. 7 illustrates an exemplary embodiment of a quick-disconnect coupling suitable for use in the tubing set of the present invention.

With respect to FIG. 7, illustrative quick-disconnect coupling 85 is described. Coupling 85 preferably comprises an rigid material such as acrylic, ABS, polysulfone or polycarbonate material and includes male portion 86 and female portion 87 that snap fit together to provide a fluid-tight seal. Male portion 86 includes silicone O-ring 88 and barb 89 for coupling to tubing. Female portion 87 includes barb 90 and release knob 91. Quick-disconnect couplings of the type illustrated in FIG. 7 are available from Colder Products Company, St. Paul, Minn., under the MPC and MPX Series connectors, although one of skill in the art will recognize that other types of quick-disconnect couplings also are suitable for use in the tubing set of the present invention.

Although preferred illustrative embodiments of the present invention are described above, it will be evident to one skilled in the art that various changes and modifications may be made without departing from the invention. It is intended that the appended claims cover all such changes and modifications that fall within the true spirit and scope of the invention.

What is claimed is:

1. A tubing set for use with a blood handling system having a blood pump/oxygenator, the tubing set having a blood inlet port and a blood outlet port, the tubing set comprising:

a perfusion circuit having a venous line configured to be coupled to an inlet of the blood pump/oxygenator, an arterial line configured to be coupled to an outlet of the blood pump/oxygenator, and a perfusion line that provides unrestricted fluid communication between the venous line and the arterial line during priming, the perfusion line adapted to be separated to form first and second free ends; and a priming circuit having a first end coupled to the venous line, a second end coupled to the arterial line and a priming line coupled between the first and second ends.

2. The tubing set of claim 1, wherein the venous line is connected to a first end of the perfusion line by a quick-disconnect coupling, and the arterial line is connected to a second end of the perfusion line by a quick-disconnect coupling.

3. The tubing set of claim 1, wherein the perfusion line includes a quick-disconnect coupling to facilitate connecting the perfusion line to the patient's circulatory system.

4. The tubing set of claim 1 wherein at least one of the venous line and the arterial line includes a valve.

5. The tubing set of claim 4 wherein the valve comprises a pinch valve.

6. The tubing set of claim 1 wherein the priming circuit further comprises at least one valve.

7. The tubing set of claim 6 wherein the valve comprises a pinch valve.

8. The tubing set of claim 1 wherein the priming line is bifurcated to form two segments.

9. The tubing set of claim 1 wherein the priming line further comprises at least one valve.

10. The tubing set of claim 9 wherein the valve comprises a pinch valve.

11. The tubing set of claim 1 wherein the perfusion line comprises tubing having an inner diameter of ⅜ inch.

12. The tubing set of claim 1 wherein the priming lines comprises tubing having an inner diameter of ¼ inch.

13. The tubing set of claim 1 wherein the priming circuit and the venous line and arterial line of the perfusion circuit have a standard length, and the perfusion line has one of a plurality of selectable lengths.

14. The tubing set of claim 1 wherein a first portion of the perfusion circuit is packaged in an inner sterile bag, and a second portion of the perfusion circuit, the inner sterile bag, and the priming circuit are enclosed in an outer sterile bag.

15. The tubing set of claim 1 wherein an aggregated length of the priming circuit, the venous line and the arterial line is no greater than 4 feet.

16. The tubing set of claim 1 wherein a length of the perfusion line is no greater than 8 feet.

* * * * *